United States Patent
Bilotti et al.

(10) Patent No.: US 7,422,138 B2
(45) Date of Patent: Sep. 9, 2008

(54) ELLIPTICAL INTRALUMINAL SURGICAL STAPLER FOR ANASTOMOSIS

(75) Inventors: Federico Bilotti, LT (IT); George M. Pomeroy, Cincinnati, OH (US); Todd P. Omaits, Liberty Township, OH (US); Laszlo Csiky, Huszar (HU); Mark A. Neurohr, Newport, KY (US); Alessandro Pastorelli, Rome (IT)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 11/344,542

(22) Filed: Feb. 1, 2006

(65) Prior Publication Data
US 2007/0175963 A1    Aug. 2, 2007

(51) Int. Cl.
*A61B 17/04*    (2006.01)
(52) U.S. Cl. ...................... 227/179.1; 227/19
(58) Field of Classification Search ............. 227/179.1, 227/175.1, 176.1, 180.1, 181.1, 19
See application file for complete search history.

(56) References Cited

U.S. PATENT DOCUMENTS

| | | | |
|---|---|---|---|
| 5,104,025 | A | 4/1992 | Main et al. |
| 5,309,927 | A | 5/1994 | Welch |
| 5,360,154 | A * | 11/1994 | Green ................. 227/179.1 |
| 5,404,870 | A * | 4/1995 | Brinkerhoff et al. ........ 600/184 |
| 5,411,508 | A * | 5/1995 | Bessler et al. ............. 606/153 |
| 6,053,390 | A * | 4/2000 | Green et al. ............. 227/179.1 |
| 6,302,311 | B1 * | 10/2001 | Adams et al. ............ 227/176.1 |
| 6,582,452 | B2 * | 6/2003 | Coleman et al. ............ 606/213 |
| 6,726,694 | B2 * | 4/2004 | Blatter et al. ............. 606/139 |
| 6,820,791 | B2 * | 11/2004 | Adams ................. 227/180.1 |
| 6,957,758 | B2 * | 10/2005 | Aranyi ................. 227/176.1 |
| 7,122,044 | B2 * | 10/2006 | Bolduc et al. ............. 606/219 |
| 2001/0004697 | A1 | 6/2001 | Blatter et al. |
| 2003/0018236 | A1 | 1/2003 | Adams |
| 2003/0144675 | A1 | 7/2003 | Nicolo |
| 2004/0004105 | A1 * | 1/2004 | Jankowski ............. 227/176.1 |
| 2004/0097994 | A1 | 5/2004 | Blatter |
| 2004/0176786 | A1 | 9/2004 | Edoga et al. |
| 2005/0187576 | A1 * | 8/2005 | Whitman et al. ............ 606/219 |
| 2005/0189397 | A1 * | 9/2005 | Jankowski ............. 227/176.1 |
| 2006/0079917 | A1 * | 4/2006 | Nicolo ................. 606/153 |
| 2006/0167485 | A1 * | 7/2006 | Blatter ................. 606/153 |
| 2006/0201989 | A1 * | 9/2006 | Ojeda ................. 227/175.1 |
| 2007/0034666 | A1 * | 2/2007 | Holsten et al. ........... 227/176.1 |
| 2007/0034667 | A1 * | 2/2007 | Holsten et al. ........... 227/176.1 |

FOREIGN PATENT DOCUMENTS

| | | |
|---|---|---|
| EP | 885595 | 12/1998 |
| EP | 1316290 | 6/2003 |
| WO | WO 2004/037064 | 5/2004 |

* cited by examiner

*Primary Examiner*—Stephen F Gerrity
(74) *Attorney, Agent, or Firm*—Welsh & Flaxman LLC

(57) ABSTRACT

A surgical stapler includes a head in which a plurality of staples are stored. The head includes a facing surface. The stapler also includes an anvil having an anvil surface shaped and dimensioned for forming the staples upon actuation of the surgical stapler, the anvil including a facing surface opposed to the facing surface of the head for mating engagement therewith. The facing surface of the head is obliquely oriented relative to a longitudinal axis of the head creating an elliptical staple line when the head is brought into contact with anvil during actuation of the surgical stapler.

10 Claims, 7 Drawing Sheets

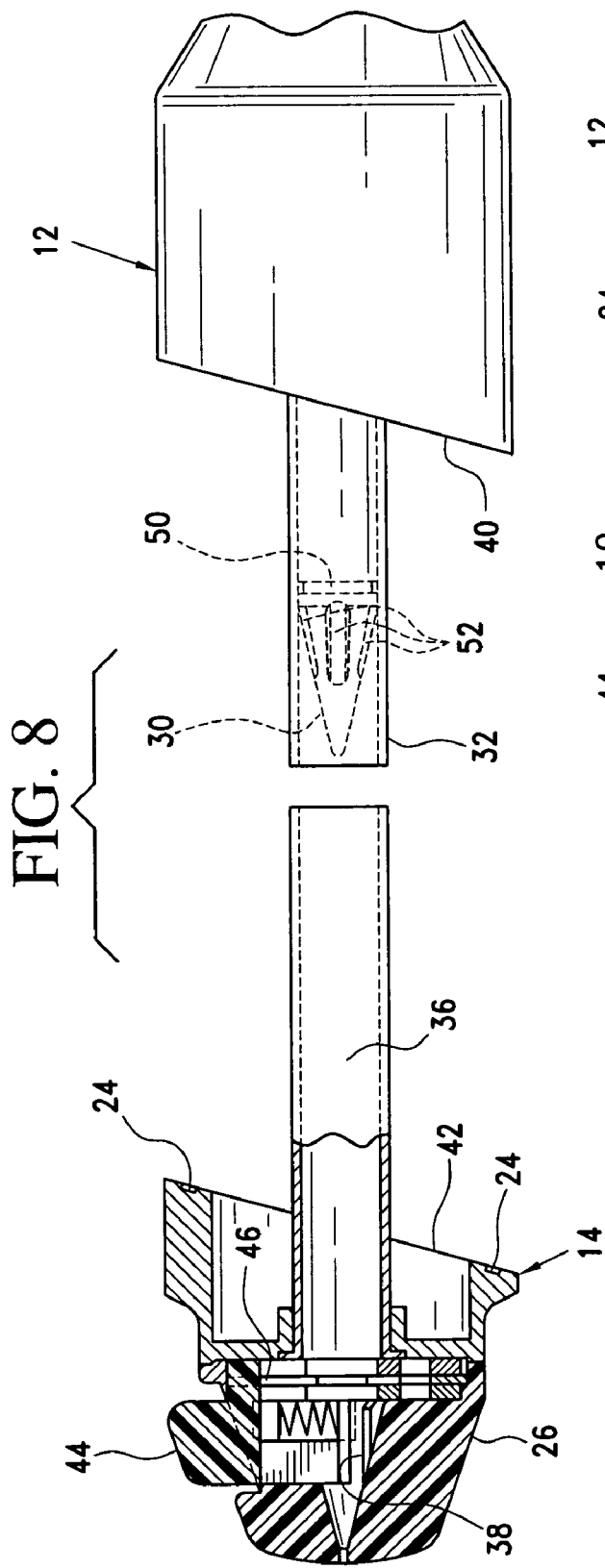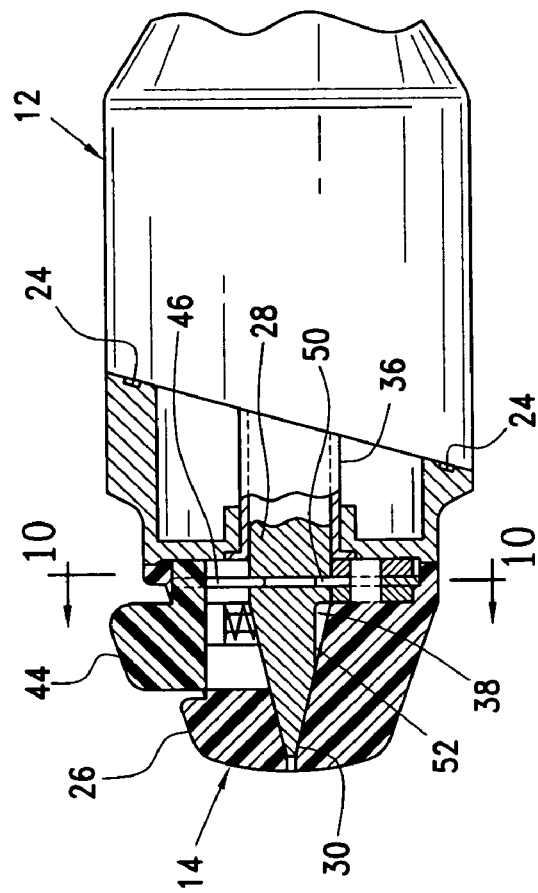

ELLIPTICAL INTRALUMINAL SURGICAL STAPLER FOR ANASTOMOSIS

BACKGROUND OF THE INVENTION

1. Field of the Invention

The invention relates to a surgical stapler for anastomosis. More particularly, the invention relates to an intraluminal surgical stapler providing for the creation of an elliptical profile during anastomosis.

2. Description of the Prior Art

Surgical staplers have long been known in the surgical art as a quick and efficient way of joining or repairing tissue. Stapling has become an acceptable alternative to suturing. In certain types of surgical procedures, the use of surgical staples has become the preferred method of joining tissue and specially configured surgical staplers have been developed for these applications.

Intraluminal, or circular, staplers, have been developed for use in surgical procedures known as anastomosis. An example of an intraluminal surgical stapler used in performing anastomosis is disclosed in U.S. Pat. No. 5,104,025, which is incorporated herein by reference.

Conventional intraluminal surgical staplers typically include an elongated shaft having a proximal actuating mechanism and a distal stapling mechanism mounted to the shaft. The distal stapling mechanism typically includes a fixed stapling cartridge containing a plurality of staples configured in a concentric circular array. A round cutting knife is concentrically mounted in the cartridge interior to the staples. The knife is moved in an axial, distal direction during operation. Extending axially from the center of the cartridge is a trocar shaft. The trocar shaft is movable axially, with respect to the cartridge. An anvil member is mounted to the trocar shaft. The anvil member has a conventional staple anvil surface mounted to it for forming the ends of the staples. The distance between the distal face of the staple cartridge and the staple anvil surface can be controlled by an adjustment mechanism mounted to the proximal end of the trocar shaft. The tissue contained between the staple cartridge and the staple anvil surface is simultaneously stapled and cut when the actuating mechanism is triggered by the surgeon.

As briefly discussed above, an anastomosis involves a surgical procedure wherein sections of intestine are joined together after a connecting section has been excised. The procedure requires joining the ends of two tubular sections together to form a continuous tubular pathway. Prior to the introduction of intraluminal surgical staplers, the surgical procedure was a laborious and time-consuming procedure. The surgeon had to precisely cut and align the ends of the intestine and maintain the alignment while joining the ends of the tubular sections with numerous suture stitches. The development of intraluminal surgical staplers has greatly simplified the anastomosis procedure and also decreased the time required to perform an anastomosis.

When performing an anastomosis using an intraluminal surgical stapler, the intestine is typically stapled using a conventional surgical stapler with double rows of staples being positioned on either side of the target section of intestine. After removing the specimen, the surgeon typically inserts the anvil of the intraluminal surgical stapler into the proximal end of the lumen, proximal of the staple line. This is done by inserting the anvil into an entry port cut into the proximal lumen by the surgeon. On occasion, the anvil can be placed transanally by placing the anvil on the distal end of the stapler and inserting the instrument through the rectum. The surgeon then ties the proximal end of the intestine to the anvil shaft using a suture or other conventional tying device. The surgeon then cuts excised tissue adjacent to the tie and the surgeon attaches the anvil to the trocar shaft of the intraluminal surgical stapler. Next the surgeon closes the gap between the anvil and cartridge, thereby engaging the proximal and distal ends of the intestine in the gap. The surgeon next actuates the intraluminal surgical stapler causing several rows of staples to be driven through both ends of the intestine thereby joining the ends and forming a tubular pathway. Simultaneously, as the staples are driven and formed, a concentric circular blade is driven through the intestine tissue, cutting the ends adjacent to the inner row of staples. The surgeon then withdraws the stapler from the intestine and the anastomosis is complete.

By creating the staple line of the newly formed lumen along a plane perpendicular to the longitudinal axis of the lumen, substantial stresses occur within the lumen. In particular, material passing through the lumen is confronted with all edges of the staple line simultaneously. This results in great stresses along the staple line. In addition, the strength of the staple line is limited by the diameter and, thus the circumference, of the lumen at the point of the staple line.

With this in mind, a need currently exists for a mechanism that optimizes the strength and functionality of a staple line created by an intraluminal surgical stapler. The present invention provides such an apparatus.

SUMMARY OF THE INVENTION

It is, therefore, an object of the present invention to provide an elliptical surgical stapler including a head in which a plurality of staples are stored. The head includes a facing surface. The surgical stapler also includes an anvil having an anvil surface shaped and dimensioned for forming the staples upon actuation of the surgical stapler, the anvil including a facing surface opposed to the facing surface of the head for mating engagement therewith. The facing surface of the head is obliquely oriented relative to the longitudinal axis of the head creating an elliptical staple line when the head is brought into contact with the anvil during actuation of the surgical stapler.

It is also an object of the present invention to provide a surgical stapler including a head in which a plurality of staples are stored. The head includes a facing surface. The surgical stapler also includes an anvil including an anvil surface shaped and dimensioned for forming the staples upon actuation of the surgical stapler, the anvil including a facing surface opposed to the facing surface of the head for mating engagement therewith. The facing surfaces of the anvil and head define an oblique mating plane on which the anvil and head create an elliptical staple line due to angled elliptical profiles of the anvil and the head.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 8 is a side view in partial cross-section of the anvil taken along lines 8-8 of FIG. 2.

FIG. 9 is a side view in partial cross-section of a closed anvil shaft seated upon a trocar tip as described in the present invention.

DESCRIPTION OF THE PREFERRED EMBODIMENTS

Figure 1:
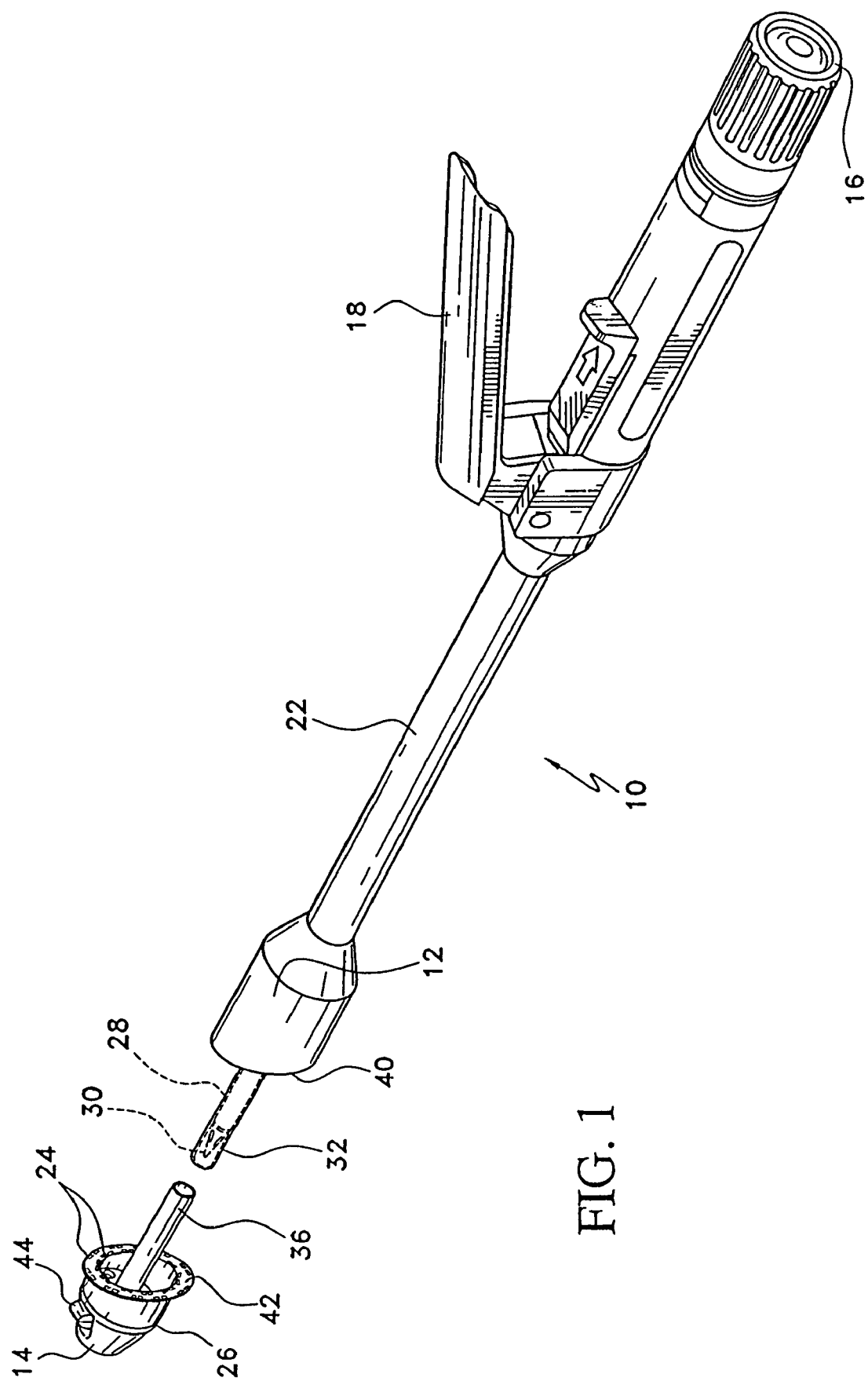
FIG. 1 is a perspective view of a surgical stapler of the present invention.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to the various figures, an intraluminal surgical stapler 10 in accordance with the present invention is disclosed. The surgical stapler 10 is substantially similar in structure and operation to intraluminal anastomotic surgical staplers such as those disclosed in commonly owned U.S. Pat. Nos. 5,104,025 to Main et al., entitled "INTRALUMINAL ANASTOMOTIC SURGICAL STAPLER WITH DETACHED ANVIL", and 5,309,927 to Welch, entitled "CIRCULAR STAPLER TISSUE RETENTION SPRING METHOD", both of which are incorporated herein by reference. While a preferred stapler design is disclosed in accordance with a preferred embodiment, the concepts underlying the present invention could be applied to a variety of stapler designs without departing from the spirit of the present invention. For example, it is contemplated the present invention could equally be applied to a stapler employing a detachable or non-detachable anvil. As those skilled in the art will appreciate, the term intraluminal surgical stapler is meant to refer to a class of surgical staplers designed to apply staples in a ring about the entire circumference of a vessel or organ during an anastomosis.

In general, the surgical stapler 10 includes a head 12, an anvil 14, an adjusting screw 16 and a trigger 18. The trigger 18 acts to operate the stapler 10 when the safety is released. When the trigger 18 is activated, a firing mechanism (not shown) operates within the shaft 22 so staples are expelled from the head 12. These staples are clinched about anvil surfaces 24 positioned circumferentially about the anvil body 26. Simultaneously, a knife 13 (shown in broken lines) held within the head 12 acts to cut tissue held within the circumference of the surgical stapler 10 between the anvil 14 and the head 12. The stapler 10 is then pulled through the tissue leaving stapled tissue in its place.

Figure 2:
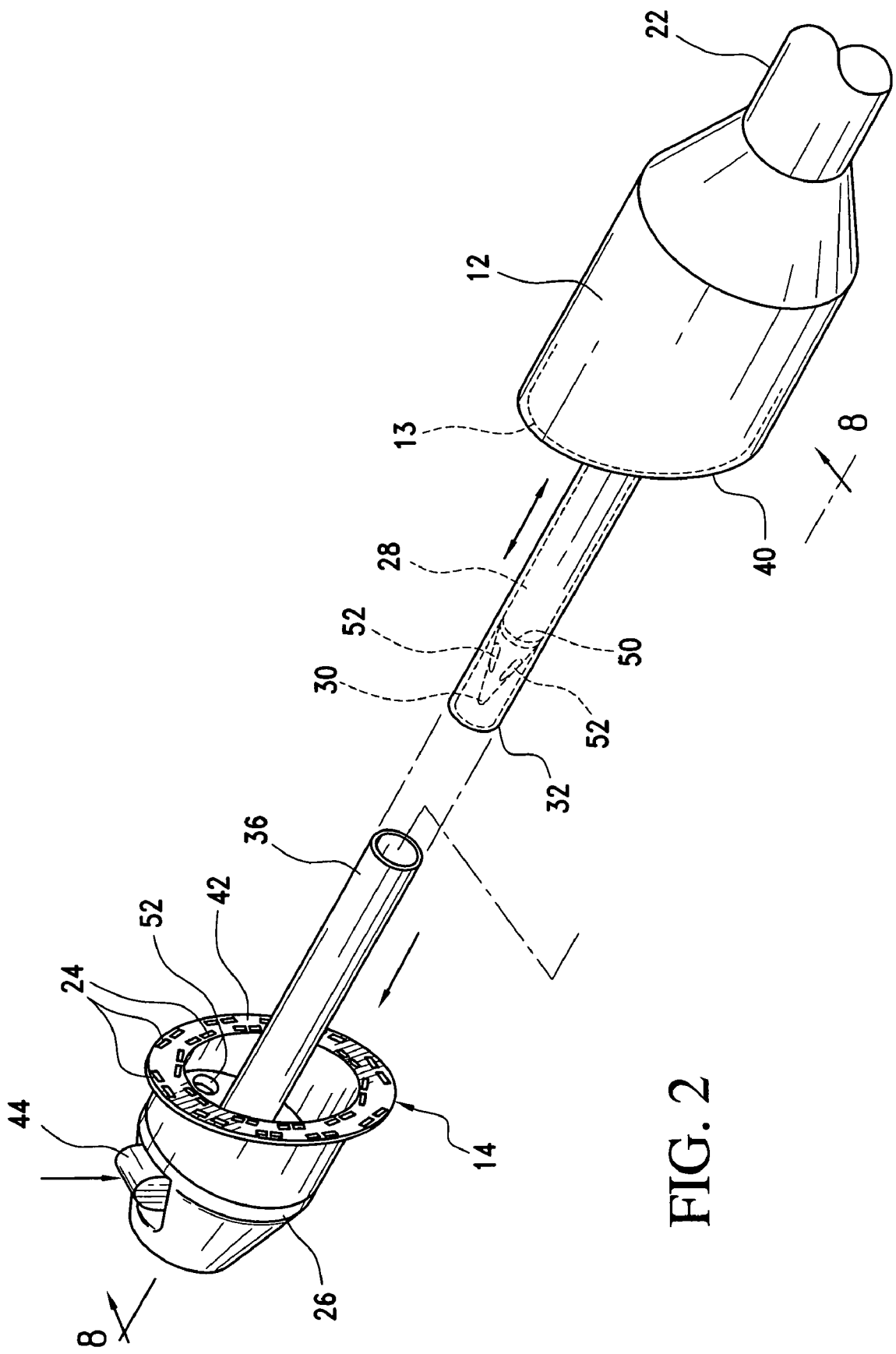
FIG. 2 is a perspective view of the head and anvil portion of a surgical stapler of the present invention.
Figure 7:
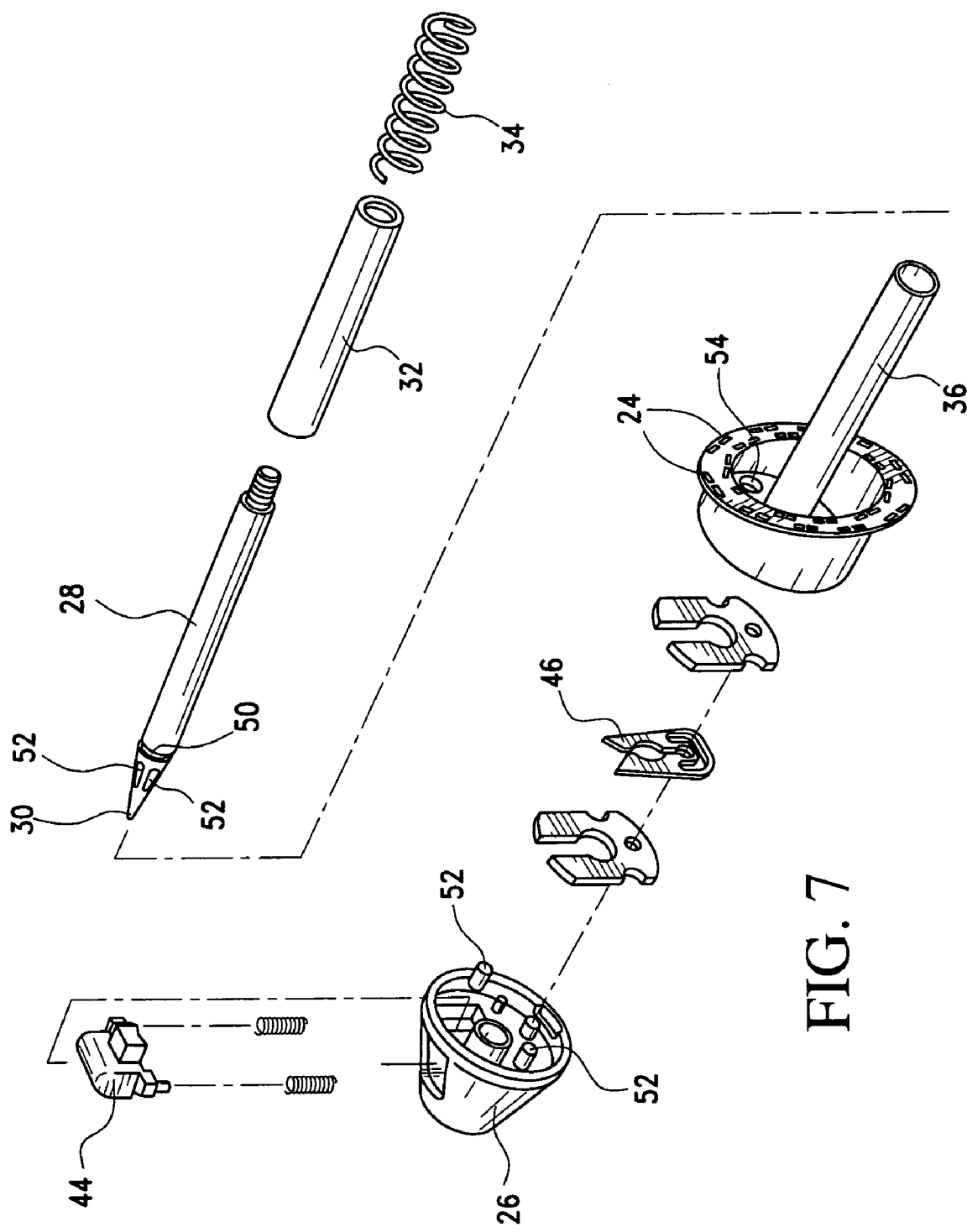
FIG. 7 is an exploded perspective view of an anvil, anvil shaft and trocar of the present invention.

As seen in FIGS. 1, 2 and 7, the surgical stapler 10 of the present invention is disclosed. More specifically, as seen in FIGS. 1 and 2, there is shown a trocar shaft 28 containing a trocar tip 30. The trocar shaft 28 is integral to the head 12 and is capable of piercing tissue. The trocar shaft 28 is surrounded by a trocar sleeve 32 that reciprocates into and out of the head 12. The trocar sleeve 32 is held on the head 12 by a spring 34 that creates its resiliency and allows reciprocation of the trocar sleeve 32 about the trocar shaft 28.

Figure 3:
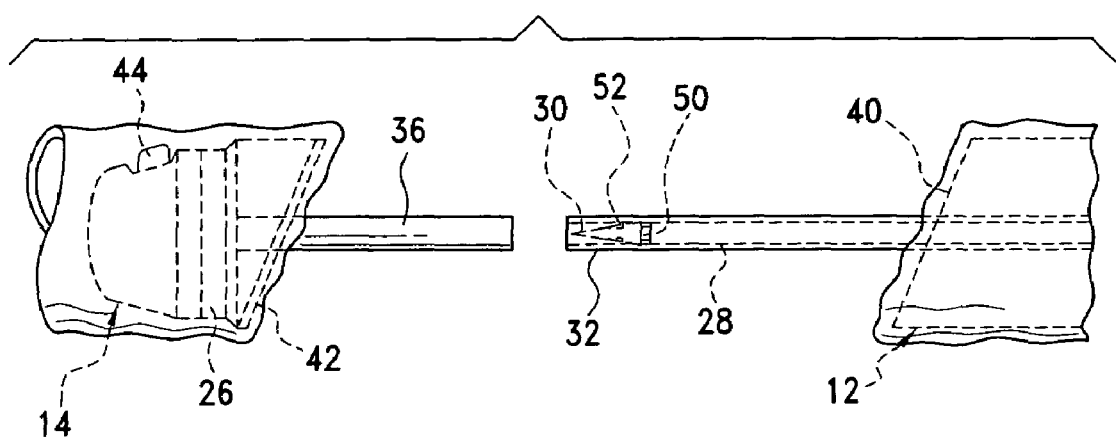
FIGS. 3, 4, 5 and 6 are side views of a closing and stapling operation of the present invention.
Figure 11:
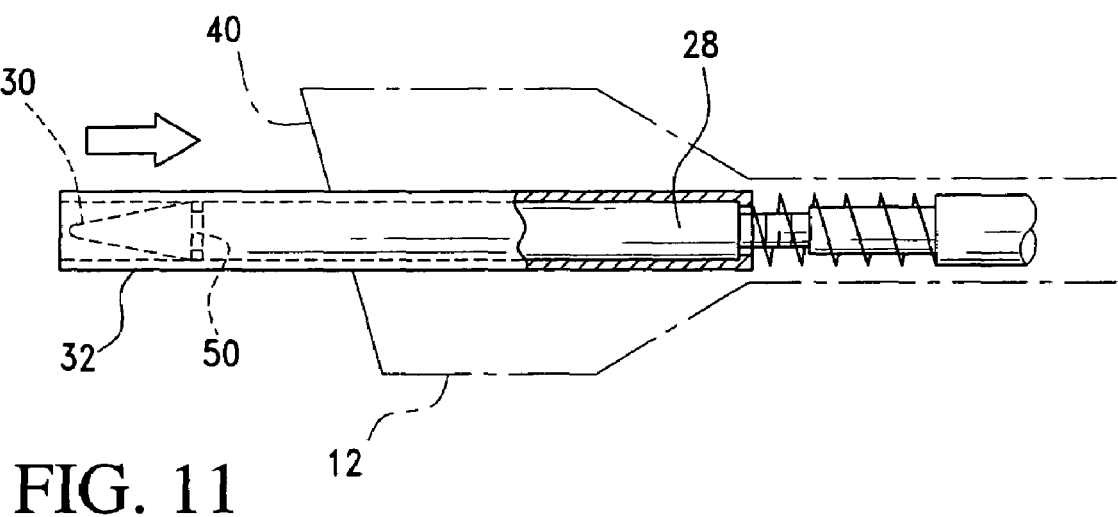
FIG. 11 is a partial cut away side view of a trocar sheathing mechanism contained in the head portion of the present invention.

As seen in FIGS. 3 and 11, the trocar shaft 28 is generally covered by the sleeve 32 so that purse-stringed tissue may be placed over the trocar sleeve 32. Nonetheless, the trocar tip 30 is capable of puncturing through tissue when pressure is applied. This is especially useful when connecting purse-stringed tissue. In this way, the trocar sleeve 32, with the trocar tip 30 exposed, is capable of being forced through a purse-stringed tissue so the purse-string is not broken. After the trocar sleeve 32 is forced through the tissue, the trocar sleeve 32 surrounds the trocar tip 30 so no further damage will be done and, yet, the lumen is adequately attached over the trocar sleeve 32.

Corresponding to the trocar shaft 28, trocar tip 30 and trocar sleeve 32, there is the anvil 14. As mentioned above, the anvil 14 includes anvil surfaces 24 positioned circumferentially around the anvil body 26. The anvil surfaces 24 correspond to staples held circumferentially within the head 12. As will be noticed in FIG. 3, the anvil 14 may be placed within a lumen of tissue, and then the tissue purse-stringed about the anvil shaft 36. An alignment mechanism (see FIG. 8) is contained within the anvil 14. As shown in FIG. 8, serrations 38 are formed along the anvil body 26. These serrations 38 correspond with indentations or recesses 52 contained on the trocar tip 30. When the anvil 14 is placed over trocar shaft 28, the serrations 38 find corresponding recesses 52 and, therefore, are able to align the anvil surfaces 24 with the staples placed circumferentially about the head 12.

In accordance with first and second embodiments of the present invention, the respective elliptical, annular facing surfaces 40, 40', 42, 42' of the head 12, 12' and anvil 14, 14' are oriented at an oblique angle relative to the longitudinal axis of the lumen through which they are passing. In the case of a surgical stapler having a straight supporting shaft with a longitudinal axis (see FIGS. 1 through 11), the facing surface 40, 42 of the head 12 and anvil 14 are oriented at an oblique angle relative to the longitudinal axis of the supporting trocar shaft 28. By orienting the facing surfaces 40, 42 of the head 12 and anvil 14 in this way, the resulting cut edges of the tissue acted upon by the present surgical stapler 10 are actually elliptically oriented when viewed normal to the cutting plane.

Since an elliptical ring cut obliquely to the longitudinal axis of a lumen will have greater surface area than a circle cut perpendicular to the same lumen, the cut surfaces created in accordance with the present invention provide for greater surface area in the stapling of adjacent tissue. This results in stronger coupling of the adjacent sections of the lumen and reduced interferences as bodily fluids pass by the cut surfaces of the lumen.

With reference to FIGS. 1 through 11, and in accordance with a first embodiment of the present invention, respective distal and proximal ends of the head 12 and anvil 14 are formed with angled facing surfaces 40, 42 defining an oblique mating plane on which the anvil 14 and head 12 will meet. By employing the angled facing surfaces 40, 42 in this manner, an elliptical staple line is created due to the tilting elliptical profiles of the proximal end of the anvil 14 and the distal end of the head 12. The arc of the ellipse is a function of the inverse cosine of the angle of the tilt, and those skilled in the art will appreciate that the ellipse may be enlarged and\or reduced by simply altering the angle at which the respective proximal and distal facing surfaces 40, 42 of the head 12 and anvil 14 lie. In other words, the more the tilt, the greater the area of the ellipse and, therefore, the greater the area of the lumen left by the device.

Those skilled in the art will certainly appreciate that the specific staples are not disclosed in accordance with the disclosure of present invention. However, it should be understood that it is preferred that the staples exit the head perpendicularly from the facing surface of the head so that they meet the anvil perpendicularly to its facing surface. This way the staples can remain symmetrically constructed while allowing variable opening of the mouth of the instrument and still meet the anvil when fired. Such a design will require that the trocar also exits the instrument (where the staples exit from the head) and meets the anvil perpendicularly from the angled cut surface (where the pockets of the anvil are formed).

Figure 13:
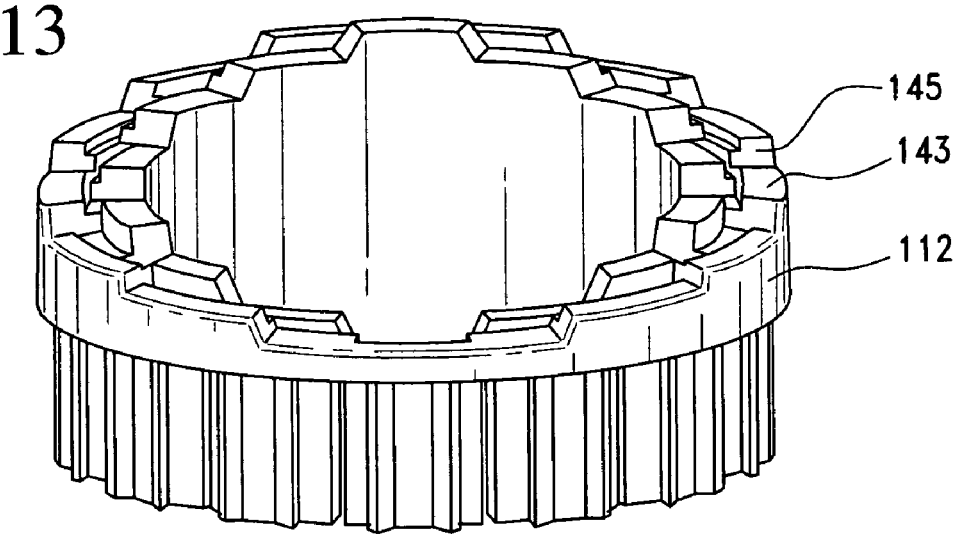
FIGS. 13 and 14 are detail views of the head and anvil in accordance with a preferred embodiment.
Figure 14:
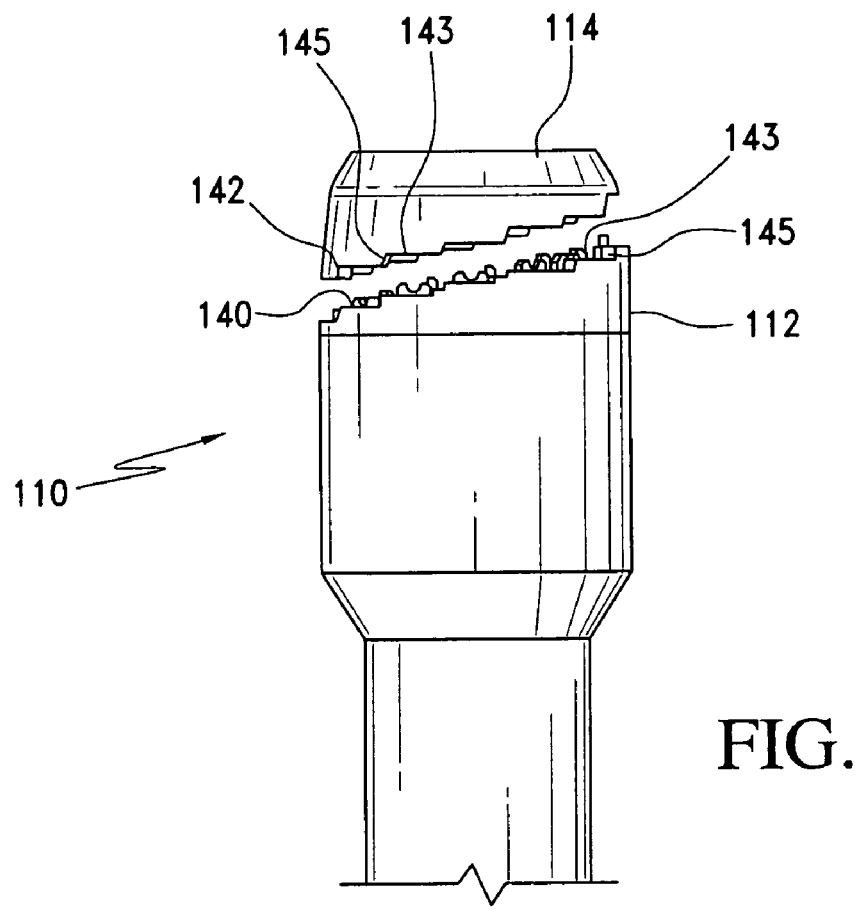

With this in mind, and in accordance a preferred embodiment of the present invention as disclosed with reference to FIGS. 13 and 14, the mating surfaces of the anvil 114 and head 112 are stepped, or otherwise offset, to create the elliptical surface desired in accordance with the present invention. More particularly, the respective distal and proximal ends of the head 112 and anvil 114 are formed with angled facing surfaces 140, 142 defining an oblique mating plane on which the anvil 114 and head 112 will meet. The angled facing surfaces 140, 142 respectively include a stepped construction composed of a series of lands 143 and risers 145. The lands 143 and risers 145 extend about the respective angled facing surfaces 140, 142 in a manner creating a facing surface which lies in a plane which is obliquely oriented relative to the longitudinal axis of the surgical stapler 110.

The staples used in accordance with this embodiment exit the head 112 in a direction perpendicular to the land 143 with which it is associated and form against the land 143 of the anvil 114 aligned therewith. As a result, the use of a stepped configuration addresses the staple formation concerns mentioned above by providing staple actuation which is oriented perpendicular to the contact surface of the anvil 114 and exit surface of the head 112.

As discussed above, by employing the angled facing surfaces 140, 142 in this manner, an elliptical staple line is created wherein the arc of the ellipse is a function of the inverse cosine of the angle of the tilt. The use of a stepped construction further enhances the ability of the head 112 and anvil 114 to reliably and consistently close based upon the proper alignment of the lands 143 and risers 145 making up the angled facing surfaces 140, 142.

Although a stepped surface is disclosed above in accordance with a preferred embodiment of the present invention, those skilled in the art will appreciate other offset constructions achieving an elliptical configuration may be employed without departing from the spirit of the present invention.

Figure 12:
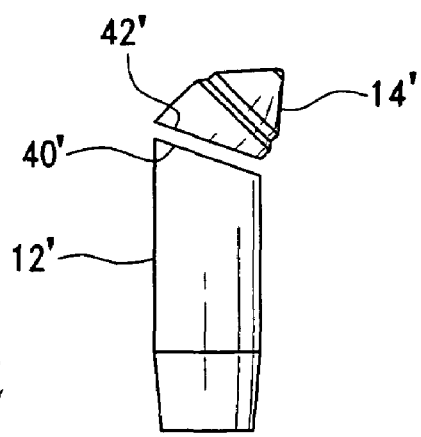
FIG. 12 is a schematic of an alternate embodiment in accordance with the present invention.

Referring to FIG. 12, the elliptical shape offered in accordance with the present invention may also be provided by tilting the entire distal end of the stapler such that the head 12' and anvil 14' meet in a plane which is obliquely oriented relative to the longitudinal axis of the shaft of the stapler 10'. More particularly, the elliptical, annular facing surface 40' at the distal end of the head 12' is oriented obliquely to the longitudinal axis of the lumen through which it is passing and to the longitudinal axis of the head 12' as a whole. The elliptical, annular facing surface 42' at the proximal end of the anvil 14' is oriented obliquely to the longitudinal axis of the lumen through which it is passing but is perpendicular to the longitudinal axis of the anvil 14' itself. As such, the anvil 14' is moved into contact with the head 12' along a line substantially perpendicular to the plane in which the facing surface 42' along the distal end of the head 12' lies.

Figure 4:
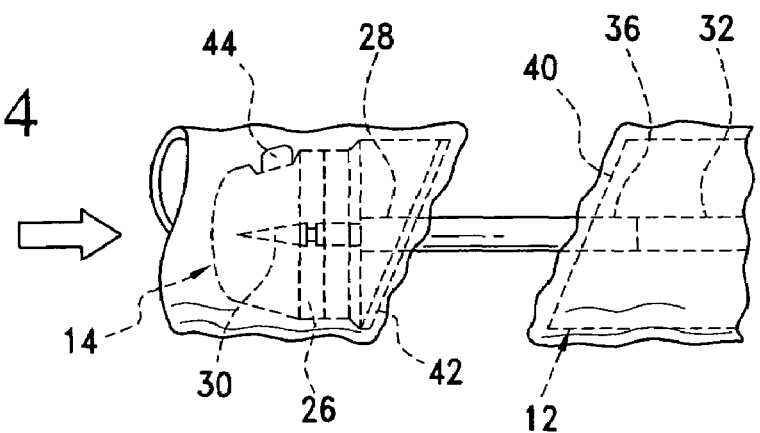
Figure 5:
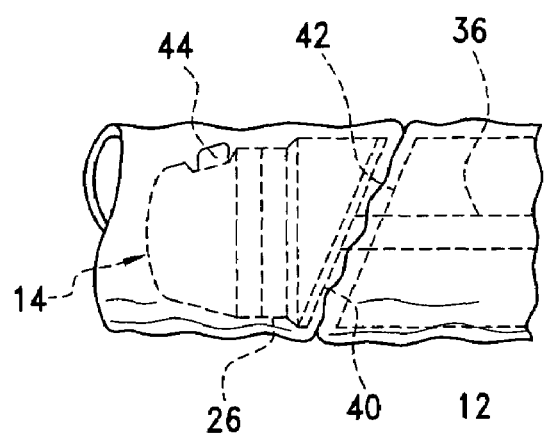

In operation as seen in FIGS. 3, 4, 5 and 6, the anvil 14 with two lumens attached to both the trocar shaft 28 and tubular anvil extension 36, respectively, is ready for surgery. As seen in FIG. 4, the anvil 14 is placed onto the trocar shaft 28 such that the trocar tip 30 is exposed and fits within the anvil shaft 36. The trocar sleeve 32 is pushed to an exposed position so it is telescoped within the head 12. When the trocar is adequately seated within the anvil head 26, locking clip 46, which contains the wedge shape spring, is caused to open and then grip about the indentation 50. Because the recesses 52 have aligned themselves with serrations 38 in the trocar shaft 28, it is ensured that the anvil surfaces 24 are aligned with the staples contained in the head 12. As better seen in FIG. 7, the serrations 38 have been aligned with the anvil surfaces 24 during manufacture through accurate placement of bosses 52 into holes 54 when connecting the anvil head 26 to the tubular anvil extension 36. The instrument now appears as two proximate pieces of lumen, as in FIG. 5. The adjusting screw 16 then pulls the tissue closer to each other.

Figure 6:
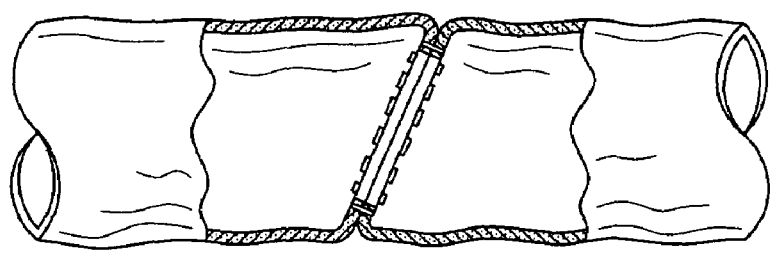

As seen in FIG. 6, the staples have been fired into the anvil surfaces 24 through the tissue. Once the staples are clinched, a knife 13 cuts tissue held within the circumference of the staples. Once this cutting occurs the stapler 10 is pulled in the direction of the head 12 and through the lumen so that a circumferentially closed lumen with an inner tubular opening is now created.

Figure 10:
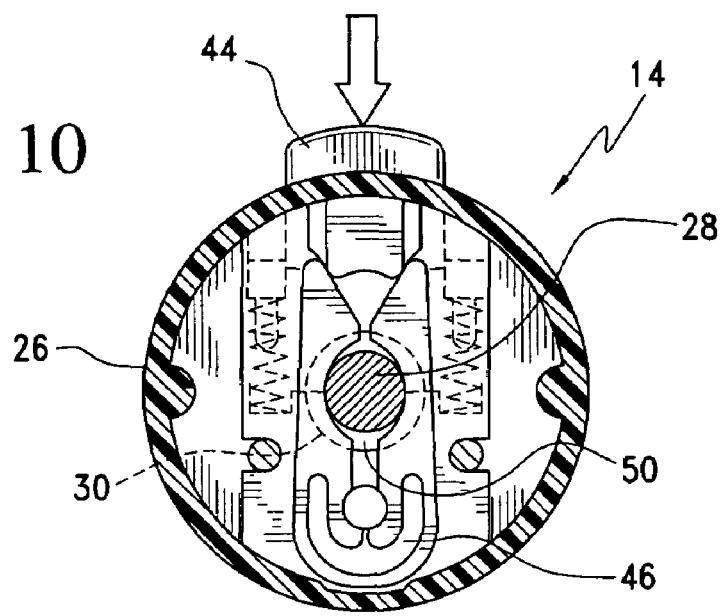
FIG. 10 is a cross-sectional top view of an anvil shaft taken along lines 10-10 of FIG. 9.

After removing the stapler 10, the excess lumen held in the stapler 10 is disposed. The release 44 on anvil 14 is pressed, as seen in FIGS. 2 and 10. This causes the locked mechanism as seen in FIG. 9 to open as alluded to in FIG. 7. The locking clip 46 now opens, allowing the user to slide the anvil shaft 36 from the stapler head 12. The tissue is held within the anvil 14 and head 12 is then removed.

In this way there has been proper purse-stringing and puncture by the trocar shaft 28, alignment between the recesses 52 and the serrations 38, pull through of the anvil body 26, the locking clip 46 about the indention, and proper stapling and cutting of the tissue.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. An elliptical surgical stapler for cutting a ring obliquely oriented relative to a longitudinal axis of a lumen, comprising:
   a head in which a plurality of staples are stored, the head including an annular facing surface;
   an anvil coupled to the head including an anvil surface shaped and dimensioned for forming the staples upon actuation of the surgical stapler, the anvil including an annular facing surface opposed to the annular facing surface of the head for mating engagement therewith, and upon mating engagement the annular facing surface of the anvil and the annular facing surface of the head define a mating plane;
   the annular facing surface of the anvil includes a stepped configuration composed of a series of lands and risers alternately extending about the circumference of the annular facing surface of the anvil to define a proximal most section along the circumference of the annular facing surface of the anvil which is diametrically opposed to a distal most section with the lands and risers extending about the circumference to link the proximal most section to the distal most section in a manner orienting the annular facing surface of the anvil in a plane obliquely oriented relative to a longitudinal axis of the surgical stapler and the annular facing surface of the head includes a stepped configuration composed of a series of lands and risers extending about the annular facing surface of the head to define a distal most section along the circumference of the annular facing surface of the head which is diametrically opposed to a proximal most section with the lands and risers extending about the circumference to link the distal most section to the proximal most section in a manner orienting the annular facing surface of the head in a plane obliquely oriented relative to a longitudinal axis of the surgical stapler; and wherein the mating plane is obliquely oriented relative to a longitudinal axis of the head creating an elliptical staple line when the head is brought into contact with the anvil during actuation of the surgical stapler.

2. The elliptical surgical stapler according to claim 1, further including a knife held within the head for cutting tissue held between the anvil and the head.

3. The elliptical surgical stapler according to claim 1, wherein the annular facing surface of the anvil is oriented at an oblique angle relative to a longitudinal axis of the anvil.

4. An elliptical surgical stapler, comprising:

a head in which a plurality of staples are stored, the head including an annular facing surface;

an anvil coupled to the head including an anvil surface shaped and dimensioned for forming the staples upon actuation of the surgical stapler, the anvil including an annular facing surface opposed to the annular facing surface of the head for mating engagement therewith;

the annular facing surface of the anvil includes a stepped configuration composed of a series of lands and risers alternately extending about the circumference of the annular facing surface of the anvil to define a proximal most section along the circumference of the annular facing surface of the anvil which is diametrically opposed to a distal most section with the lands and risers extending about the circumference to link the proximal most section to the distal most section in a manner orienting the annular facing surface of the anvil in a plane obliquely oriented relative to a longitudinal axis of the surgical stapler and the annular facing surface of the head includes a stepped configuration composed of a series of lands and risers extending about the annular facing surface of the head to define a distal most section along the circumference of the annular facing surface of the head which is diametrically opposed to a proximal most section with the lands and risers extending about the circumference to link the distal most section to the proximal most section in a manner orienting the annular facing surface of the head in a plane obliquely oriented relative to a longitudinal axis of the surgical stapler; and wherein upon mating engagement the annular facing surface of the anvil and the annular facing surface of the head define an oblique mating plane on which the anvil and head create an elliptical staple line due to angled elliptical profiles of the facing surfaces of the anvil and the head.

5. The elliptical surgical stapler according to claim 4, further including a knife held within the head for cutting tissue held between the anvil and the head.

6. The elliptical surgical stapler according to claim 4, wherein the annular facing surface of the head is oriented at an oblique angle relative to a longitudinal axis of the head.

7. The elliptical surgical stapler according to claim 6, wherein the annular facing surface of the anvil is oriented at an oblique angle relative to a longitudinal axis of the anvil.

8. The elliptical surgical stapler according to claim 4, wherein the annular facing surface of the anvil is oriented at an oblique angle relative to a longitudinal axis of the anvil.

9. An intraluminal surgical stapler, comprising:

a head in which a plurality of staples are stored, the head including an elliptical, annular facing surface;

an anvil coupled to the head including an anvil surface shaped and dimensioned for forming the staples upon actuation of the surgical stapler, the anvil including an elliptical, annular facing surface opposed to the facing surface of the head for mating engagement therewith, and upon mating engagement the annular facing surface of the anvil and the annular facing surface of the head define a mating plane;

the annular facing surface of the anvil includes a stepped configuration composed of a series of lands and risers alternately extending about the circumference of the annular facing surface of the anvil to define a proximal most section along the circumference of the annular facing surface of the anvil which is diametrically opposed to a distal most section with the lands and risers extending about the circumference to link the proximal most section to the distal most section in a manner orienting the annular facing surface of the anvil in a plane obliquely oriented relative to a longitudinal axis of the surgical stapler and the annular facing surface of the head includes a stepped configuration composed of a series of lands and risers extending about the annular facing surface of the head to define a distal most section along the circumference of the annular facing surface of the head which is diametrically opposed to a proximal most section with the lands and risers extending about the circumference to link the distal most section to the proximal most section in a manner orienting the annular facing surface of the head in a plane obliquely oriented relative to a longitudinal axis of the surgical stapler; and wherein the mating plane is obliquely oriented relative to a longitudinal axis of the head.

10. The elliptical surgical stapler according to claim 9, further including a knife held within the head for cutting tissue held between the anvil and the head.

* * * * *